United States Patent [19]

Imai et al.

[11] Patent Number: 5,128,241

[45] Date of Patent: Jul. 7, 1992

[54] MICROCAPSULE IMMUNOASSAY AND REAGENTS THEREFOR

[75] Inventors: Kyoko Imai, Katsuta; Yasushi Nomura, Mito, both of Japan

[73] Assignee: Hitachi, Ltd., Tokyo, Japan

[21] Appl. No.: 140,117

[22] Filed: Dec. 31, 1987

[30] Foreign Application Priority Data

Feb. 6, 1987 [JP] Japan ................................. 62-24473

[51] Int. Cl.$^5$ .......................................... G01N 33/544
[52] U.S. Cl. ...................... 435/7.7; 435/7.72; 435/7.9; 435/7.93; 435/18; 435/966; 435/975; 436/519; 436/520; 436/528; 436/821; 436/829
[58] Field of Search .................... 435/7, 18, 810, 975, 435/7.72, 7.7, 7.9, 7.93, 966; 436/519, 520, 528, 821, 829

[56] References Cited

U.S. PATENT DOCUMENTS

| | | | |
|---|---|---|---|
| 4,483,921 | 11/1984 | Cole | 435/7 |
| 4,707,441 | 11/1987 | Ahmad et al. | 436/829 |

FOREIGN PATENT DOCUMENTS

| | | |
|---|---|---|
| A0103139 | 3/1984 | European Pat. Off. |
| A0132556 | 2/1985 | European Pat. Off. |
| 3618100 | 12/1986 | Fed. Rep. of Germany |
| 28661 | 2/1984 | Japan |
| 159652 | 8/1985 | Japan |
| 176855 | 8/1986 | Japan |
| 269070 | 11/1986 | Japan |
| 277062 | 12/1986 | Japan |
| 110155 | 5/1987 | Japan |
| A2069133 | 8/1981 | United Kingdom |

OTHER PUBLICATIONS

Clinical Chemistry, vol. 31, No. 9, Sep. 1985, "A highly sensitive immunoassay system involving anitbody-coated tubes and liposome-entrapped dye", J. P. O'Connel et al., pp. 1424-1426.

W. M. Hunter, in D. M. Weir (ED), *Handbook Of Experimental Immunology*, Blackwell Scientific Publications, Oxford, 1978, pp. 14.25-14.26.

HSIA et al, *Ann. N.Y. Acad. Sci.*, 308, 139-148, 1978.

*Primary Examiner*—David Saunders
*Attorney, Agent, or Firm*—Fay, Sharpe, Beall, Fagan, Minnich & McKee

[57] ABSTRACT

Microcapsule-reagents are prepared by previously reacting at least a part of an antigen or antibody attached to microcapsules encapsulating a labeling substance with an antibody or antigen which is specifically reactive therewith, and then the reagent thus prepared is reacted with a sample containing an antigen or antibody in the presence of a complement, whereby highly sensitive immunoassay of the antigen or antibody in the sample can be realized even when the antigen or antibody attached to the microcapsules has a lowered activity or has only low reactivity with the antibody or antigen in the sample.

28 Claims, 1 Drawing Sheet

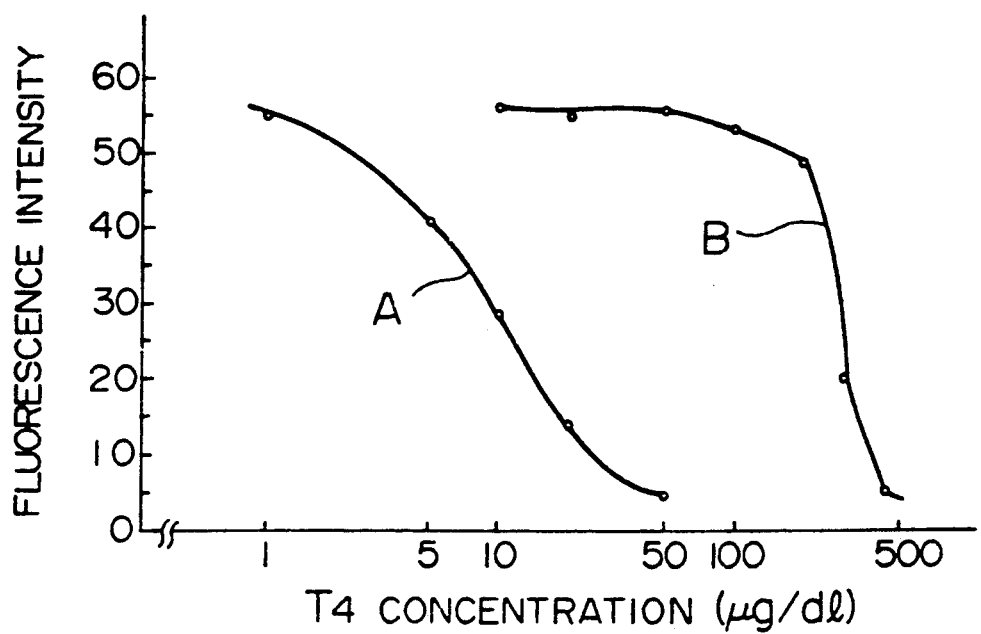
F I G. 1
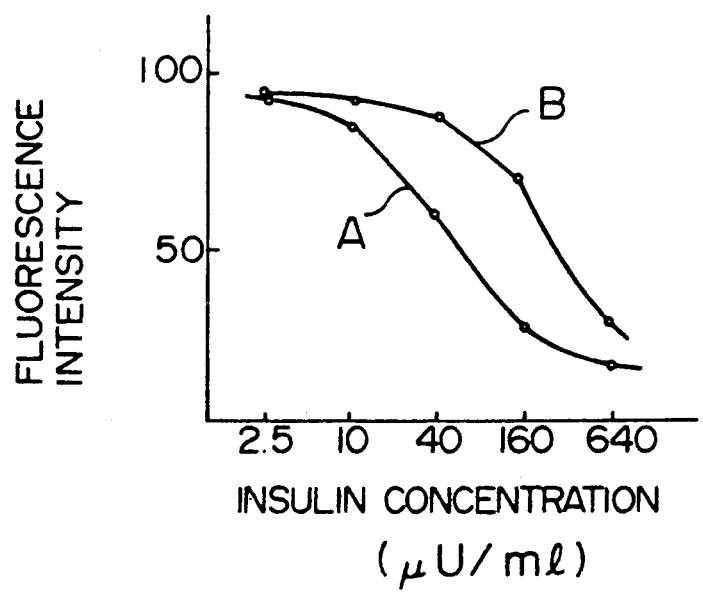
F I G. 2

MICROCAPSULE IMMUNOASSAY AND REAGENTS THEREFOR

BACKGROUND OF THE INVENTION

1. Field of the Invention

This invention relates to a method for immunoassay and reagents therefor, particularly to a method for immunoassay and a kit therefor which are suitable for quantitating a specific antigen or antibody present in a sample.

2. Related Art Statement

Radioimmunoassay (RIA) has heretofore been used in order to quantitate sample components with high sensitivity. However, RIA is disadvantageous in that handling of isotopes used therein such as their storage and disposal is troublesome, and therefore analytical methods which can be employed in place of RIA have been investigated.

For example, U.S. Pat. No. 4,483,921 discloses a method for immunoassay using lipid molecular membrane (as microcapsules, e.g., liposomes) having an antigen or antibody attached thereto.

An analytical method using microcapsules comprises encapsulating a labeling substance such as enzyme, fluorescent substance or luminous substance, and a precursor thereof in microcapsules, measuring the amount of the labeling substance released by destruction of the liposomes by antigen-antibody reaction, and thereby determining the concentration of a substance to be assayed.

As another example of this kind of analytical method, Japanese Patent Kokai (Laid-Open) No. 28661/84 discloses an immunoassay method comprising using sheep erythrocyte membrane as microcapsules, encapsulating an enzyme or a substrate into the microcapsules, and quantitating an antigen or an antibody by utilizing enzymatic reaction, and discloses reagents for immunoassay which are used for said immunoassay method.

In both of the methods described above, the same antigen or antibody as the substance to be assayed is attached to the surface of microcapsules. In all the conventional analytical methods using an antigen or antibody attached to microcapsules which is the same as a substance to be assayed, a so-called competitive reaction is utilized in which an antigen or antibody attached to microcapsules and an antigen or antibody in a sample react competitively with an antibody or antigen added as a reagent.

However, study by the present inventors has revealed that when a fat-soluble antigen is attached on microcapsules, the antigencity becomes lower in some cases.

Furthermore, when antigen is a protein, it is often attached on microcapsules by use of a bifunctional crosslinking agent such as glutaraldehyde, and it has been found that when attached on microcapsules by use of such a crosslinking agent, the protein is lowered in antigenic activity in some cases.

For these reasons, destruction of microcapsules (e.g., liposomes) by antigen-antibody reaction at the time of the competitive reaction becomes difficult to occur, resulting in a marked lowering of the detection sensitivity of assay and an increase of the required reaction time in some cases.

It has also been found that when the origin of an antigen attached to microcapsules is different from that of an antibody used for the reaction, the reaction activity and hence the detection sensitivity of assay are, in some cases, lower than when their origins are the same.

For example, when a substance to be assayed is one which is difficult to be synthesized or is per se expensive such as human insulin, an antigen from a different origin is often used in place of an antigen having the same origin. That is to say, in determining human insulin, bovine insulin can be attached to microcapsules and used for the reaction.

However, the following phenomenon has been confirmed by the present inventors. When the microcapsules having bovine insulin attached thereto and human insulin in a sample are competitively reacted with an anti-human insulin antibody which is highly reactive with human insulin in the sample, bovine insulin is less reactive with anti-human insulin antibody than human insulin, resulting in difficulty of destruction of the microcapsules.

On the other hand, as a method for immunoassay which is different from the competitive reaction method, Japanese Patent Kokai (Laid-Open) No. 269070/86 discloses a method which comprises covalently binding an antibody to liposomes encapsulating a labeling substance, reacting the resulting antibody-sensitized liposomes and free antibody with an antigen in a sample to obtain a sandwich type antigen-antibody complex, and thereby quantitating the antigen in the sample. However, this method is also disadvantageous in that the activity of the antibody bound to the liposomes is lowered, so that the determination sensitivity is lowered.

In addition, Japanese Patent Kokai (Laid-Open) No. 159652/85 discloses a method which comprises attaching a second antibody against a first antibody to microcapsules encapsulating a labeling substance, reacting the resulting second-antibody sensitized microcapsules with the first antibody and an antigen in a sample to obtain (antigen)-(first antibody)-(second-antibody)-sensitized microcapsules, adding thereto a complement, measuring the labeling substance released, and thereby quantitating the antigen in the sample. Such a method is disadvantageous in that since various reagents such as the first antibody and the second antibody should be prepared, the method is troublesome, and that since the method involves the two reaction steps, longer time is required for the determination of the antigen in the sample and further the determination sensitivity is lowered.

SUMMARY OF THE INVENTION

This invention was made in order to solve the problems described above. An object of this invention is to provide an immunoassay method to provide highly sensitive immunoassay for quantitating antibody or antigen by use of microcapsules having antigen or antibody attached thereto, and a kit for immunoassay which can be used for said immunoassay method.

Another object of this invention is to provide a novel microcapsule reagent which can be used for said kit.

Further another object of this invention is to provide an immunoassay method which permits highly sensitive immunoassay even when the origin of an antigen or antibody attached to microcapsules is different from that of an antigen or antibody to be assayed.

Other and further objects and advantages of this invention will be apparent from the following description.

The objects described above can be achieved by attaching an antigen or antibody to microcapsules (e.g., liposomes) which undergo lysis (i.e., destruction) by complement activity or action of a divalent or higher-order polyvalent metal ion;

reacting previously at least a part of the antigen or antibody with an antibody or antigen which is reactive specifically with the antigen or antibody to prepare a new microcapsule-reagent;

adding an antibody or antigen in a sample to the microcapsule reagent; and reacting the antibody or antigen in the sample with the antigen or antibody which has reacted previously with the antibody or antigen attached to the microcapsule, in the presence of a complement or a divalent or higher-order metal ion.

That is to say, one aspect of this invention is a method for immunoassay comprising (a) a step of adding an antigen or antibody to be assayed and a reagent having lytic activity in the presence of an antigen-antibody complex to a microcapsule-reagent comprising microcapsules encapsulating a labeling substance which undergo lysis by the reagent having lytic activity in the presence of an antigen-antibody complex, an antigen or antibody attached to the surface of these microcapsules, and an antibody or antigen which is reactive specifically with the antigen or antibody, respectively, attached to the surface of the microcapsules and has reacted previously with at least a part of this antigen or antibody, respectively; and carrying out competitive reaction of the antigen or antibody attached to the surface of said microcapsules and the antigen or antibody to be assayed with the antibody or antigen, respectively, which has reacted previously with the antigen or antibody, respectively, attached to the surface of said microcapsules, and (b) a step of measuring the labeling substance released from the microcapsules by the step (a) and thereby quantitating the antigen or antibody to be assayed.

Another aspect of this invention is a method for immunoassay of human antigen or antibody comprising (a) a step of adding a human antigen or antibody to be assayed and a reagent having lytic activity in the presence of an antigen-antibody complex to a microcapsule-reagent comprising microcapsules encapsulating a labeling substance which undergo lysis by the reagent having lytic activity in the presence of an antigen-antibody complex, an antigen or antibody originated from an animal attached to the surface of these microcapsules, and a human antibody or antigen which is reactive specifically with the antigen or antibody, respectively, attached to the surface of the microcapsules and has reacted previously with at least a part of this antigen or antibody, respectively; and carrying out competitive reaction of the antigen or antibody attached to the surface of said microcapsules and the antigen or antibody to be assayed with the antibody or antigen, respectively, which has reacted previously with the antigen or antibody, respectively, attached to the surface of said microcapsules, and (b) a step of measuring the labeling substance released from the microcapsules by the step (a) and thereby quantitating the antigen or antibody to be assayed.

Further another aspect of this invention is a kit for immunoassay for quantitating antigen or antibody by competitive reaction comprises (a) a microcapsule-reagent comprising microcapsules encapsulating a labeling substance which undergo lysis by a reagent having lytic activity in the presence of an antigen-antibody complex, an antigen or antibody attached to the surface of these microcapsules, and an antibody or antigen which is reactive specifically with the antigen or antibody, respectively, attached to the surface of the microcapsules and has reacted previously with at least a part of this antigen or antibody, respectively; and (b) a reagent having lytic activity in the presence of an antigen-antibody complex.

Still another aspect of this invention is a microcapsule-reagent comprising microcapsules encapsulating a labeling substance which undergo lysis by a reagent having lytic activity in the presence of an antigen-antibody complex, an antigen or antibody attached to the surface of these microcapsules, and an antibody or antigen which is reactive specifically with the antigen or antibody, respectively, attached to the surface of the microcapsule and has reacted previously with at least a part of this antigen or antibody, respectively.

This invention is a method for quantitating antigen or antibody, previously allowing to react at least a part of antigen or antibody attached to microcapsules with an antibody or antigen reactive specifically therewith to prepare a microcapsule-reagent with an antigen-antibody complex on its surface, then adding a sample containing an antigen or antibody and a complement or a divalent or higher-order polyvalent metal ion to the reagent, and carrying out competitive reaction of the antigen or antibody in the sample and the antigen or antibody attached to the microcapsules with the previously reacted antibody or antigen, namely, bringing the antigen or antibody in the sample and the antigen or antibody attached to the microcapsules into competition with each other (based on antigen-antibody reaction) for the previously reacted antibody or antigen. According to this invention, highly sensitive immunoassay of an antigen or antibody in a sample can be realized even when the antigen or antibody attached to the microcapsules has a lowered activity or has only low reactivity with the antibody or antigen in the sample.

BRIEF DESCRIPTION OF THE DRAWINGS

FIG. 1 is a graph showing one example of calibration curve for quantitating Thyroxin ($T_4$) in one Example of this invention. FIG. 2 is a graph showing one example of calibration curve for quantitation of human insulin according to this invention.

DETAILED DESCRIPTION OF THE INVENTION

Substances which can be quantitated by the immunoassay method of this invention include very various substances, for example, antigens such as tumor markers (e.g., α-fetoprotein), immunoglobulins, thyroid hormones (e.g., thyroxin), insulin, etc., and antibodies corresponding thereto.

The labeling substance encapsulated in the microcapsules may be any one so long as it is a hydrophilic substance which can be quantitated when released from the microcapsules, or a precursor thereof. Therefore, the term "labeling substance" used in the present specification is defined so as to include a precursor thereof. As such a labeling substance, preferable are, for example, fluorescent substances such as carboxyfluorescein, etc.; high-absorbing compounds such as water-soluble dyes, etc.; sugars such as glucose, sucrose, etc.; ionic compounds such as tetrapentylammonium, etc.; enzymes such as glucose oxidase, etc. (see Japanese Patent Kokai (Laid-Open) No. 28661/84); coenzymes such as NAD, etc.; radical compounds such as methylviologen, etc.; and chelating agents such as 5-bromo-2-pyridylazo-5-N-propyl-N-sulfopropylaminoaniline (see Japanese Patent Kokai (Laid-Open) No. 176855/86).

The microcapsule includes liposomes, erythrocyte ghost membrane, etc.; and among them, liposomes are preferred.

The reagent having lytic activity in the presence of an antigen-antibody complex includes complements and divalent or higher-order polyvalent metal ions. As the complements, there are usually used, for example, guinia pig serum. As the divalent or higher-order polyvalent metal ions, there are used, for example, magnesium ion, manganese ion, calcium ion, etc., and the concentration of these metal ions at the time of the reaction is suitably 3 mM to 20 mM (see Japanese Patent Kokai (Laid-Open) No. 277062/86).

Production of the reagent for immunoassay of this invention and the immunoassay method using this reagent are practiced, for example, in the following manners.

First, microcapsules having an antigen attached thereto which is the same as an antigen to be assayed, are prepared by a conventional method (see, for example, Japanese Patent Kokai (Laid-Open) No. 28661/84). The antigen (or antibody) may be attached to microcapsules through a crosslinking agent such as SPDP (N-succinimidyl-3-(2-pyridylthio)propionate), SMPB (N-succinimidyl-4-(p-maleimidophenyl)butyrate) or the like. Next, a suitable amount of an antibody reactive specifically with the antigen is added and reacted sufficiently with the antigen attached to the surface of the microcapsules.

Finally, the unreacted antibody is removed by centrifuge to obtain microcapsules on which at least a part of the antigen attached to the surface has reacted previously with the antibody, namely, the microcapsule-reagent with an antigen-antibody complex on its surface.

In the microcapsule reagent with an antigen-antibody complex on its surface. Thus obtained, it is not always necessary that the whole of the antigen attached to the surface of the microcapsules has reacted with the antibody added afterward, although the higher the proportion of the antigen which has reacted with the antibody, the higher the sensitivity of immunoassay.

Highly sensitive assay aimed at by this invention is made possible by adding a sample containing an antigen to the microcapsule-reagent together with a complement or a divalent or higher-order polyvalent metal ion to subject this antigen and the antigen on the surface of the microcapsule to competitive reaction with the previously reacted antibody, measuring the amount of a labeling substance released from the microcapsules, and quantitating the antigen in the sample by using a calibration curve previously prepared by use of reagents with known concentrations.

The microcapsule-reagent of this invention can be obtained also by, in contrast with the production process of the reagent described above, first preparing microcapsules having an antibody attached thereto, and then adding thereto an antigen reactive specifically with the antibody to obtain the antibody-antigen reaction.

Furthermore, in this invention, a human antigen or antibody can be assayed with high sensitivity, for example, by attaching an antigen originated from an animal to microcapsules, then reacting a human antibody reactive specifically with this antigen to obtain microcapsule-reagent, and adding thereto a sample containing a human antigen to subject the human antigen and the animal antigen attached to microcapsules to competitive reaction with the human antibody.

According to such an analytical method, a human antigen or antibody can be assayed very economically.

This invention is further explained below in more detail with reference to Examples.

EXAMPLE 1

Microcapsules are composed of, for example, small particles made of lipid thin membrane, and an antigen is attached to the surface of the microcapsules. A method for preparing such microcapsules is disclosed, for example, by Hsia et al. [Method in Enzymology, 74, 152 (1981)].

A fluorescent substance, carboxyfluorescein was introduced as a labeling substance into the above-mentioned microcapsules, and Thyroxin ($T_4$) was attached to the surface of the microcapsules. To 500 $\mu l$ of the microcapsules thus prepared was added 100 $\mu l$ of anti-$T_4$ antibody, and the resulting mixture was incubated at room temperature for 2 hours.

Next, 1 ml of Veronal buffer (pH 7.4) was added, after which centrifuge was conducted at a rotation rate of 15,000 r.p.m. for 30 minutes and the supernatant was removed. This procedure was repeated three times to remove the unreacted antibody. The precipitate thus obtained was suspended in 500 ml of the same buffer as described above to prepare a microcapsule-reagent suspension, which was used in reaction with a sample (containing an antigen to be assayed, i.e., Thyroxin).

To 173 $\mu l$ of the same buffer as described above were added 2 $\mu l$ of the microcapsule-reagent suspension thus obtained, 20 $\mu l$ of a test sample and 5 $\mu l$ of a complement solution (guinea pig serum), and the resulting mixture was incubated at room temperature for 30 minutes. The $T_4$ concentration in the sample was determined by measuring the intensity of fluorescence of carboxyfluorescein which had flowed out of the microcapsules owing to destruction of the microcapsules by the antigen-antibody reaction.

For the determination of $T_4$ concentration in the sample, a calibration curve previously prepared was used. Calibration curve for quantitating $T_4$ obtained by a conventional competitive reaction method and calibration curve obtained by the method of this invention are shown by B and A, respectively, in FIG. 1.

As can be seen from FIG. 1, a $T_4$ concentration range where fluorescence intensity changes with $T_4$ concentration is 1 to 40 $\mu g/dl$ in the case of using the reagent and the immunoassay method of this invention, while it is 100 to 500 $\mu g/dl$ in the case of using conventional reagent and analytical method. From these measurement results, it can be seen that the analytical method of this invention is much more sensitive than the conventional method.

EXAMPLE 2

Microcapsules (liposomes) having, as antigen, bovine insulin attached thereto were obtained in the same manner as in Example 1. As in Example 1, carboxyfluorescein was introduced into the microcapsules.

To 500 $\mu l$ of the microcapsules thus prepared was added 200 $\mu l$ of anti-human insulin antibody and the resulting mixture was incubated at room temperature for 1 hour. The unreacted antibody was removed by centrifuge, and then the residue was suspended in 500 μl of Veronal buffer (pH 7.4).

To 143 μl of the same buffer as described above were added 2 μl of the microcapsules thus prepared, 50 μl of a sample and 5 μl of a complement solution (guinea pig serum), and the resulting mixture was incubated at room temperature for 30 minutes. The fluorescence intensity of the reaction mixture was measured in the same manner as in Example 1, whereby the human insulin concentration in the sample could be determined.

Calibration curves in Example 2 are shown in FIG. 2, in which A shows a calibration curve obtained by the method of this invention and B that obtained by a conventional method.

As described above, according to this invention, a highly sensitive immunoassay method can be provided even when the microcapsule-sensitizing antigen has a lowered antigenicity or has only low reactivity with the antigen.

What is claimed is:

1. A method for immunoassay, comprising the steps of:
   providing a sample having one of an antigen and antibody to be assayed;
   providing a reagent having lytic activity in the presence of an antigen-antibody complex on the surface of a microcapsule-reagent;
   providing a previously prepared microcapsule-reagent comprising microcapsules having a surface, a labeling substance encapsulated in the microcapsules, and a corresponding one of an antigen and antibody completely reacted with a corresponding amount of the other of an antigen and antibody to form an antigen-antibody complex on the surface of the microcapsules substantially without any unreacted other of an antigen and antibody;
   after all of said steps of providing, adding together the sample, the reagent having lytic activity and the microcapsule-reagent having the antigen-antibody complex;
   competitively reacting the one of the antigen and antibody of the sample and the corresponding one of the antigen and antibody of the antigen-antibody complex with the other of the antigen and antibody of the antigen-antibody complex on at least some of the microcapsule-reagent to remove the antigen-antibody complex from the surface of the some of the microcapsule reagent, thereby leaving the remainder of the microcapsule-reagent with the antigen-antibody complex on its surface;
   releasing the labeling substance from the microcapsules of the remainder of the microcapsule-reagent by the lytic activity of the reagent having lytic activity substantially without releasing the labeling substance of the some of the microcapsule-reagent having antigen-antibody complex removed from its surface due to said competitively reacting step; and
   measuring the labeling substance released from the microcapsules and thereby quantitating the one of the antigen and antibody to be assayed on the sample in inverse proportion to the quantity of released labeling substance.

2. The immunoassay method according to claim 1, wherein said step of providing said microcapsule-reagent includes attaching one of the antigen or antibody to the surface of the microcapsule by a cross-linking reagent and thereafter, prior to said step of adding, reacting the other of the antibody or antigen with the antigen or antibody on the microcapsule to provide the antigen antibody complex on the surface of the microcapsule to thereby provide the microcapsule reagent.

3. The method for immunoassay according to claim 1, wherein the reagent having lytic activity in the presence of an antigen-antibody complex is complement.

4. The method of immunoassay according to claim 3, wherein said step of providing a microcapsule reagent includes:
   providing the microcapsules encapsulating the labeling substance with the one of antigen and antibody on the surface of the microcapsules;
   providing the other of the antigen and antibody in excess of a quantity of the one of the antigen and antibody on the surface of the microcapsules;
   reacting the other of the antigen and antibody with the one of the antigen and antibody to provide the antigen-antibody complex on the surface of the microcapsules; and
   removing the excess of unreacted other of the antigen and antibody to thereby provide the microcapsule reagent.

5. The method for immunoassay according to claim 1, wherein the reagent having lytic activity in the presence of an antigen-antibody complex is a divalent or higher-order polyvalent metal ion.

6. The method for immunoassay according to claim 5, wherein said step of providing a microcapsule reagent includes:
   providing the microcapsules encapsulating the labeling substance with the one of antigen and antibody on the surface of the microcapsules;
   providing the other of the antigen and antibody in excess of a quantity of the one of the antigen and antibody on the surface of the microcapsules;
   reacting the other of the antigen and antibody with the one of the antigen and antibody to provide the antigen-antibody complex on the surface of the microcapsules; and
   removing the excess of unreacted other of the antigen and antibody to thereby provide the microcapsule reagent.

7. The method for immunoassay according to claim 1, wherein the microcapsule is a liposome.

8. The method for immunoassay according to claim 7, wherein said step of providing a microcapsule reagent includes:
   providing the microcapsules encapsulating the labeling substance with the one of antigen and antibody on the surface of the microcapsules;
   providing the other of the antigen and antibody in excess of a quantity of the one of the antigen and antibody on the surface of the microcapsules;
   reacting the other of the antigen and antibody with the one of the antigen and antibody to provide the antigen-antibody complex on the surface of the microcapsules; and
   removing the excess of unreacted other of the antigen and antibody to thereby provide the microcapsule reagent.

9. The method for immunoassay according to claim 1, wherein the labeling substance is selected from the group consisting of fluorescent substances, light-absorbing compounds, ionic compounds, sugars, enzymes, coenzymes, and chelating agents.

10. The method for immunoassay according to claim 9, wherein said step of providing a microcapsule reagent includes:
- providing the microcapsules encapsulating the labeling substance with the one of antigen and antibody on the surface of the microcapsules;
- providing the other of the antigen and antibody in excess of a quantity of the one of the antigen and antibody on the surface of the microcapsules;
- reacting the other of the antigen and antibody with the one of the antigen and antibody to provide the antigen-antibody complex on the surface of the microcapsules; and
- removing the excess of unreacted other of the antigen and antibody to thereby provide the microcapsule reagent.

11. The method for immunoassay according to claim 1, wherein said step of providing a microcapsule reagent includes:
- providing the microcapsules encapsulating the labeling substance with the one of antigen and antibody on the surface of the microcapsules;
- providing the other of the antigen and antibody in excess of a quantity of the one of the antigen and antibody on the surface of the microcapsules;
- reacting the other of the antigen and antibody with the one of the antigen and antibody to provide the antigen-antibody complex on the surface of the microcapsules; and
- removing the excess of unreacted other of the antigen and antibody to thereby provide the microcapsule reagent.

12. The immunoassay method according to claim 11, wherein said step of providing said microcapsule-reagent includes attaching one of the antigen or antibody to the surface of the microcapsule by a cross-linking agent and thereafter, prior to said step of adding, reacting the other of the antibody or antigen with the antigen or antibody on the microcapsule to provide the antigen antibody complex on the surface of the microcapsule to thereby provide the microcapsule reagent.

13. The immunoassay method according to claim 1, wherein said step of providing the sample provides the sample with the one of the antigen and antibody from a human source, and said step of providing the microcapsule-reagent provides at least one of the antigen or antibody of the antigen-antibody complex from an animal source.

14. The method for immunoassay according to claim 13, wherein said step of providing a microcapsule reagent includes:
- providing the microcapsules encapsulating the labeling substance with the one of antigen and antibody on the surface of the microcapsules;
- providing the other of the antigen and antibody in excess of a quantity of the one of the antigen and antibody on the surface of the microcapsules;
- reacting the other of the antigen and antibody with the one of the antigen and antibody to provide the antigen-antibody complex on the surface of the microcapsules; and
- removing the excess of unreacted other of the antigen and antibody to thereby provide the microcapsule reagent.

15. The immunoassay method according to claim 14, wherein said step of providing the microcapsule-reagent provides the antigen as a protein originated from an animal source and antibody as an anti-human protein antibody.

16. The method for immunoassay according to claim 15, wherein the anti-human protein is anti-human insulin.

17. The immunoassay method according to claim 14, wherein said step of providing said microcapsule-reagent includes attaching one of the antigen or antibody to the surface of the microcapsule by a cross-linking reagent and thereafter, prior to said step of adding, reacting the other of the antibody or antigen with the antigen or antibody on the microcapsule to provide the antigen antibody complex on the surface of the microcapsule to thereby provide the microcapsule reagent.

18. The method for immunoassay according to claim 13, wherein the reagent having lytic activity in the presence of an antigen-antibody complex is complement.

19. The method for immunoassay according to claim 18, wherein said step of providing a microcapsule reagent includes:
- providing the microcapsules encapsulating the labeling substance with the one of antigen and antibody on the surface of the microcapsules;
- providing the other of the antigen and antibody in excess of a quantity of the one of the antigen and antibody on the surface of the microcapsules;
- reacting the other of the antigen and antibody with the one of the antigen and antibody to provide the antigen-antibody complex on the surface of the microcapsules; and
- removing the excess of unreacted other of the antigen and antibody to thereby provide the microcapsule reagent.

20. The method for immunoassay according to claim 13, wherein the reagent having lytic activity in the presence of an antigen-antibody complex is a divalent or higher-order polyvalent metal ion.

21. The method for immunoassay according to claim 20, wherein said step of providing a microcapsule reagent includes:
- providing the microcapsules encapsulating the labeling substance with the one of antigen and antibody on the surface of the microcapsules;
- providing the other of the antigen and antibody in excess of a quantity of the one of the antigen and antibody on the surface of the microcapsules;
- reacting the other of the antigen and antibody with the one of the antigen and antibody to provide the antigen-antibody complex on the surface of the microcapsules; and
- removing the excess of unreacted other of the antigen and antibody to thereby provide the microcapsule reagent.

22. The method for immunoassay according to claim 13, wherein the microcapsule is a liposome.

23. The method for immunoassay according to claim 22, wherein said step of providing a microcapsule reagent includes:
- providing the microcapsules encapsulating the labeling substance with the one of antigen and antibody on the surface of the microcapsules;
- providing the other of the antigen and antibody in excess of a quantity of the one of the antigen and antibody on the surface of the microcapsules;
- reacting the other of the antigen and antibody with the one of the antigen and antibody to provide the antigen-antibody complex on the surface of the microcapsules; and removing the excess of unreacted other of the antigen and antibody to thereby provide the microcapsule reagent.

24. The method for immunoassay according to claim 13, wherein the labeling substance is selected from the group consisting of fluorescent substances, light-absorbing compounds, ionic compounds, sugars, enzymes, coenzymes, chelating agents, and methylviologen.

25. The method for immunoassay according to claim 24, wherein said step of providing a microcapsule reagent includes:

providing the microcapsules encapsulating the labeling substance with the one of antigen and antibody on the surface of the microcapsules;

providing the other of the antigen and antibody in excess of a quantity of the one of the antigen and antibody on the surface of the microcapsules;

reacting the other of the antigen and antibody with the one of the antigen and antibody to provide the antigen-antibody complex on the surface of the microcapsules; and removing the excess of unreacted other of the antigen and antibody to thereby provide the microcapsule reagent.

26. The immunoassay method according to claim 13, wherein said step of providing said microcapsule-reagent includes attaching one of the antigen or antibody to the surface of the microcapsule by a cross-linking agent and thereafter, prior to said step of adding, reacting the other of the antibody or antigen with the antigen or antibody on the microcapsule to provide the antigen antibody complex on the surface of the microcapsule to thereby provide the microcapsule reagent.

27. A method of forming a microcapsule-reagent for use in immunoassay, comprising the steps of:

providing microcapsules having a surface, a labeling substance encapsulated in the microcapsules, and one of an antigen and antibody on the surface of the microcapsules;

providing the other of the antigen and antibody in excess of a quantity of the one of the antigen and antibody on the surface of the microcapsule;

reacting the other of the antigen and antibody with the one of the antigen and antibody upon the surface of the microcapsules to provide an antigen-antibody complex on the surface of the microcapsules sufficiently so that there is substantially no unreacted one of the antigen and antibody; and removing the excess of unreacted other of the antigen and antibody to thereby provide the microcapsule reagent.

28. An immunoassay test kit for quantitating one of an antigen and antibody in a sample, said test kit comprising:

a reagent having lytic activity in the presence of an antigen-antibody complex on the surface of a microcapsule-reagent;

a microcapsule reagent comprising microcapsules having a surface, a labeling substance encapsulated in the microcapsules, and an antigen-antibody complex on the surface of the microcapsules, wherein the antigens and antibodies on the surface of the microcapsule are substantially completely reacted to form the antigen-antibody complex.

* * * * *